(12) United States Patent
Maleski et al.

(10) Patent No.: US 7,989,572 B2
(45) Date of Patent: Aug. 2, 2011

(54) POLYVINYL ULTRAVIOLET LIGHT ABSORBERS FOR PERSONAL CARE

(75) Inventors: Robert Joseph Maleski, Kingsport, TN (US); Ramesh Chand Munjal, Kingsport, TN (US); Max Allen Weaver, Kingsport, TN (US); Jean Carroll Fleischer, Kingsport, TN (US); Michael Gale Ramsey, Limestone, TN (US); Greg Alan King, Mount Carmel, TN (US); Edward Enns McEntire, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 711 days.

(21) Appl. No.: 12/015,828

(22) Filed: Jan. 17, 2008

(65) Prior Publication Data

US 2009/0185988 A1 Jul. 23, 2009

(51) Int. Cl.
  *C08F 20/00* (2006.01)
(52) U.S. Cl. .................................................. 526/303.1
(58) Field of Classification Search ................ 526/303.1
  See application file for complete search history.

(56) References Cited

U.S. PATENT DOCUMENTS

| | | | |
|---|---|---|---|
| 3,313,866 A | 4/1967 | Horton et al. | |
| 3,529,055 A | 9/1970 | Skoultchi et al. | |
| 3,943,094 A | 3/1976 | Margotte et al. | |
| 4,004,074 A | 1/1977 | Gerecht et al. | |
| 4,233,430 A | 11/1980 | Jacquet et al. | |
| 4,524,061 A | 6/1985 | Cho et al. | |
| 4,528,311 A | 7/1985 | Beard et al. | |
| 4,839,160 A | 6/1989 | Forestier et al. | |
| 5,063,048 A | 11/1991 | Saitoh et al. | |
| 5,099,027 A | 3/1992 | Vogl et al. | |
| 5,243,021 A | 9/1993 | Langer et al. | |
| 5,374,419 A | 12/1994 | Krutak et al. | |
| 5,495,039 A | 2/1996 | Frater et al. | |
| 5,698,183 A | 12/1997 | Langer et al. | |
| 5,843,410 A | 12/1998 | Kim et al. | |
| 5,864,473 A | 1/1999 | Slack et al. | |
| 5,869,099 A | 2/1999 | Keller et al. | |
| 6,068,929 A | 5/2000 | Dauth et al. | |
| 6,114,559 A | 9/2000 | Richard et al. | |
| 6,123,938 A | 9/2000 | Stern et al. | |
| 6,143,850 A | 11/2000 | Keller et al. | |
| 6,193,959 B1 | 2/2001 | Bernasconi et al. | |
| 6,887,400 B1 | 5/2005 | Wei et al. | |
| 7,008,618 B1 | 3/2006 | Hessefort et al. | |
| 7,087,692 B2 | 8/2006 | Koshti et al. | |
| 2005/0191249 A1 | 9/2005 | Bonda et al. | |
| 2006/0115516 A1* | 6/2006 | Pearson et al. | 424/428 |

FOREIGN PATENT DOCUMENTS

JP 07258166 10/1995
WO WO 2006/057824 A2 6/2006

OTHER PUBLICATIONS

Notification of Transmittal of the International Search Report and the Written Opinion of the International Searching Authority, or the Declaration date of mailing Oct. 27, 2009 received in corresponding International Application No. PCT/US2009/000066.
Wu, Shuizhu et al.; "Mesomorphous Structure and Macroscopic Patterns Formed by polymer and Surfactant from Organic Solutions"; Macromolecules; 2005; pp. 9266-9274; vol. 38.
Cosmetics and Toiletries, vol. 115, No. 6, p. 37-45 (2002).
N. A. Shaath, Cosmetics and Toiletries, 101, Mar. 1986, pp. 55-70.
Consumer Reports, Jun. 1988, pp. 370-374.
Chemical and Engineering News, Apr. 11, 2005, pp. 18-22.
Hanson et al, Free Radical Biology and Medicine, vol. 41, Issue 8, 2006, pp. 1205-1212.
Experimental Dermatology, 2000, vol. 9, pp. 165-169.
Invitation to Pay Additional Fees date of mailing May 28, 2009 received in corresponding International Application No. PCT/US2009/000066.

* cited by examiner

*Primary Examiner* — Edward J Cain
(74) *Attorney, Agent, or Firm* — Brett L Nelson; Bernard J. Graves, Jr.

(57) ABSTRACT

UV-absorbing polymers and copolymers suitable for Composition into sunscreens for the protection of human skin. The UV-absorbing chromophoric monomers chosen are simple and easily synthesized. With the correct choice of chromophoric monomer or mixture of monomers, protection against UV-A radiation or against both UV-A and UV-B radiation can be achieved. With the correct choice of comonomer, copolymers produced as aqueous latex emulsions or as Polyethylene Glycol solutions can also be achieved.

11 Claims, 3 Drawing Sheets

POLYVINYL ULTRAVIOLET LIGHT ABSORBERS FOR PERSONAL CARE

FIELD OF THE INVENTION

This invention pertains to certain novel polymeric compounds which exhibit unique ultraviolet light absorbing properties. This invention also concerns a composition including these polymer compositions which are useful for protecting human skin from the deleterious effects of ultraviolet light.

BACKGROUND OF THE INVENTION

Recently, considerable attention has been given to the observed increase in skin cancer attributed in part to people's lifestyles and leisure activities that result in excessive and prolonged exposure to harmful ultraviolet (UV) light rays present in solar radiation. The UV rays have been divided into three regions: UV-A Region (320-400 nm), UV-B Region (290-320 nm) and UV-C Region (200-290 nm). The UV-C Region has the highest energy and most damaging radiation, but is largely absorbed by the ozone layer. UV light in the UV-B Region, also called the Erythemal or Burning Region, causes sunburn and is responsible for most of the immediate damage to the human body, i.e., skin and hair. UV-A Radiation, also called the Tanning Region, causes tanning but also may cause many other harmful biological effects, such as DNA damage and the formation of dermal cysts (Cosmetics and Toiletries, Vol 115, No 6, p 37-45 (2002), and references therein).

Many Personal Care products contain materials that absorb the harmful ultraviolet light to protect the skin from damage. Early formulations of these contained UV light-absorbing chemicals capable of absorbing most of the UV-B light, but little of the UV-A light. Because of the harmful effects of UV-A radiation most formulations now include a combination of UV-A and UV-B light absorbing compounds. Because some of the active ultraviolet light absorbers are destroyed by ultraviolet radiation, many formulations contain stabilizers that also absorb ultraviolet radiation. See, for example, N. A. Shaath, Cosmetics and Toiletries, 101, March 1986, pp 55-70; Consumer Reports, June 1988, pp 370-374, and Chemical and Engineering News, Apr. 11, 2005, pp 18-22. These modern formulations have been designed to absorb most of the UV light in the range of 280 to 400 nm, particularly in the 280 to 360 nm range which contains the most damaging UV light. Modem formulations are also designed to remain stable to ultraviolet light for several hours after their application to the skin.

Many ultraviolet light absorbers for personal care are small organic molecules with molecular weights below 600 amu's. A significant body of evidence shows that many of these molecules can penetrate the skin, and recent work indicates that once this occurs—absent a reapplication of the sunscreen—their presence in the skin may cause more free-radical induced damage than that observed in untreated skin. See Hanson et al, Free Radical Biology and Medicine, Volume 41, Issue 8, 2006, pp 1205-1212.

Large molecules, on the other hand, are known not to easily penetrate the skin (Experimental Dermatology, 2000, Vol 9, pp 165-169) so polymeric ultraviolet absorbers cannot cause the cellular damage possible for ultraviolet light absorbers which are small molecules.

The objective of this invention is to provide polymeric UV absorbing materials that can absorb either UV-A radiation or a combination of UV-A and UV-B radiation, that contain a high concentration of the UV-absorbing moieties, and that do not penetrate the skin.

Polymeric ultraviolet light absorbers are known. UV-absorbing chromophores have been incorporated into polyesters (U.S. Pat. Nos. 5,243,021, 5,374,419), polyamides (U.S. Pat. No. 3,864,473), polyester-polyamide copolymers (U.S. Pat. No. 5,698,183), silicone-containing polymers (U.S. Pat. Nos. 5,495,039, 6,068,929, 6,114,559, 6,193,959), and polyaminoamides (U.S. Pat. No. 6,887,400). Polyanhydride resins have also been reacted with UV absorbers capable of reacting with anhydride moieties (US published application 20050191249 A1).

UV absorbers have also been functionalized with groups capable of undergoing a vinyl polymerization. Homopolymers (U.S. Pat. Nos. 3,313,866, 5,099,027 5,843,410) and various copolymers with maleic anhydride (U.S. Pat. No. 5,869,099), acrylic acid or its derivatives (U.S. Pat. Nos. 3,529,055, 4,233,430, 4,524,061, 4,839,160, 4,528,311, 5,063,048, 6,123,938, 7,008,618), substituted styrenes (U.S. Pat. Nos. 5,843,410, 7,087,692), vinyl esters of carboxylic acids (U.S. Pat. No. 6,143,850), and vinyl thioacetate (U.S. Pat. No. 4,004,074) have been disclosed.

All of the above polymeric ultraviolet light absorbers suffer either due to low concentration of the UV absorbing moiety in the polymer or due to the absorption of light in only a narrow portion of the UV region.

SUMMARY OF THE INVENTION

This invention relates to a UV absorbing polymer, comprising at least one residue of a chromophoric monomer structure depicted by Ia or Ib below or a combination thereof:

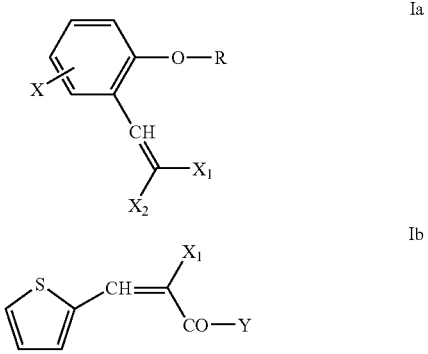

wherein X is hydrogen or one or two groups selected from the group consisting of hydroxy, $C_1$-$C_6$-alkyl, halogen, and —OR';

$X_1$ and $X_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;

R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$-alkenyl, —(CHR$_1$CHR$_2$O—)$_n$—R$_3$, and -L-Q;

wherein $R_1$ and $R_2$ are independently selected from the group consisting of hydrogen and $C_1$-$C_6$-alkyl;

$R_3$ is selected from the group consisting of hydrogen, $C_1$-$C_6$-alkyl, $C_1$-$C_6$-alkanoyl, aroyl, and aryl;

L is a divalent organic radical selected from the group consisting of $C_1$-$C_6$-alkylene-O—, $C_1$-$C_6$-alkylene-N (R₁)—, arylene-C₁-C₆-alkylene-O—, arylene-C₁-C₆-alkylene-(NR₁)—, arylene-(OCHR₁CHR₂O)$_n$—, C₁-C₆-alkylene-Y₁—(CHR₁CHR₂O—)$_n$—, and —(CHR₁CHR₂O—)$_n$—;

n is 1-1000; and

Y₁ is selected from the group consisting of —O—, —S—, —SO₂—, —N(SO₂R₄)—, and —N(COR₄)—;

Y is independently selected from the group consisting of —O-L-Q, —N(R₄)-L-Q, —N-(L-Q)₂, and —R₄;

wherein R₄ is selected from the group consisting of C₁-C₁₂-alkyl, substituted C₁-C₁₂-alkyl, C₃-C₈-cycloalkyl, C₃-C₈-alkenyl, and aryl; and Q is a group that comprises an ethylenically unsaturated polymerizable group;

with the proviso that the monomer molecules each comprise at least one Q group.

In another embodiment the polymer described above further comprising at least one residue of one chromophoric monomer structure depicted by Ic or Id below or a combination thereof.

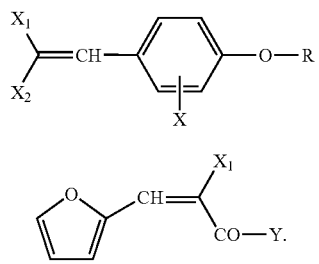

Ic

Id

Another embodiment concerns a polymeric UV absorbing composition, comprising the polymer described above, and a cosmetically acceptable carrier, wherein the polymer comprises residues of monomer Ia and residues of at least one of Ib Ic, and Id, and said residues are present in a ratio of Ia/In by weight of about 99/1 to about 60/40, where In is Ib, Ic, Id or any combination thereof.

Yet another embodiment concerns a polymeric UV absorbing composition, comprising the polymer described above and a cosmetically acceptable carrier.

Still another embodiment concerns a chromophoric monomer comprising a structure depicted by Formula Ia.

Another embodiment concerns a chromophoric monomer comprising a structure depicted by Formula Ib.

Another embodiment concerns a composition, comprising a latex emulsion and the polymer described above.

DETAILED DESCRIPTION

Definitions

Figure 1:
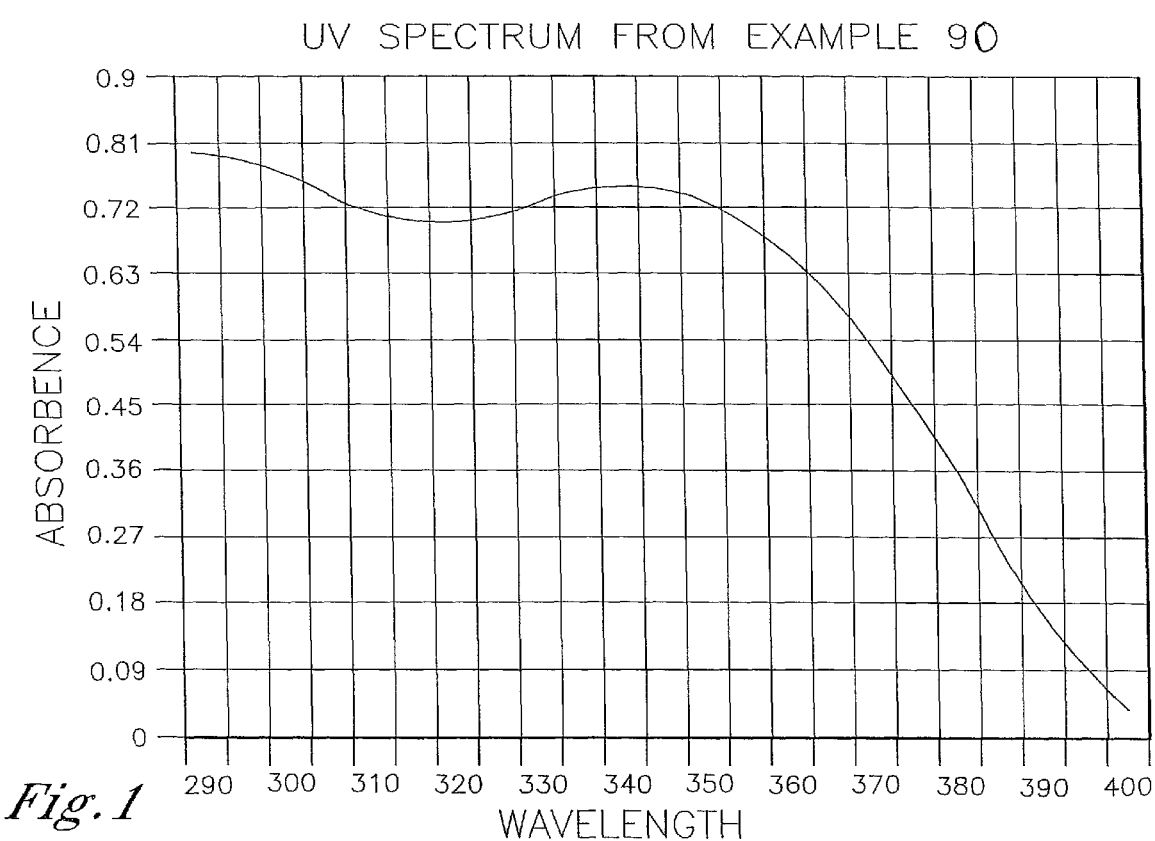
FIG. 1 shows the UV Spectrum of a Ultraviolet light absorbing composition according to the present invention.

The following definitions apply to terms as used throughout this application.

The alkyl groups described by the term "C₁-C₆-alkyl" refer to straight or branched-chain saturated hydrocarbon radicals containing one to six carbon atoms optionally substituted with one or two groups selected from hydroxy, —O-Q, cyano, aryl, aryloxy, arylthio, arylsulfonyl, —OR₁₁, —OCOR₁₁, —OCO₂—R₁₁, and —O(CH₂CH₂O)₁₋₁₀₀₀—R₁₂, wherein R₁₁ represents a saturated straight or branched chain hydrocarbon radical containing one to four carbon atoms; R₁₂ is hydrogen or is selected from —R₁₁, —COR₁₁, and —CO₂R₁₁; Q is as previously defined.

The alkyl groups described by the term "C₁-C₁₂-alkyl" refer to straight or branched chain saturated hydrocarbon radicals containing one to twelve carbon atoms.

The term "C₃-C₈-cycloalkyl" refers to a cyclic saturated hydrocarbon radical containing three to eight carbon atoms.

The term "aryl" includes phenyl and naphthyl and these radicals substituted with one to three groups selected from: C₁-C₆-alkyl, C₁-C₆-alkoxy, —CN, —NO₂, C₁-C₆-alkoxycarbonyl, C₁-C₆-alkanoyloxy, C₁-C₆-alkylsulfonyl, hydroxyl, carboxy, halogen, —O-L-Q, and —COY, wherein L, Q, and Y are as previously defined.

The term "heteroaryl" includes 5 or 6-membered heterocyclic aryl rings containing one oxygen atom, and/or one sulfur atom, and up to three nitrogen atoms, said heterocyclic aryl ring optionally fused to one or two phenyl rings. Examples of such systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl and the like; these are optionally substituted with one to three groups selected from C₁-C₆-alkyl, C₁-C₆-alkoxy, —CN, —NO₂, C₁-C₆-alkoxycarbonyl, C₁-C₆-alkanoyloxy, C₁-C₆-alkylsulfonyl, and halogen groups.

The term "substituted-C₁-C₁₂-alkyl" is used herein to denote a straight or branched chain, saturated aliphatic hydrocarbon radical containing one to twelve carbon atoms and these radicals optionally substituted with one to three groups selected from hydroxy; halogen; cyano; succinimido; glutarimido; phthalimido; 2-pyrrolidono; aryl; heteroaryl; heteroarylthio; aryloxy; arylthio; C₁-C₆-alkoxy; C₁-C₆-alkylthio; C₁-C₆-alkylsulfonyl; arylsulfonyl; o-benzoic sulfimido; C₁-C₆-alkylsulfonamido; arylsulfonamido; C₃-C₈-alkenylcarbonylamino; —OX₃R₁₃; —NHX₃R₁₃; —CONR₁₄R'₁₄; —SO₂NR₁₄R'₁₄; wherein R₁₃ is selected from C₁-C₁₂-alkyl and C₁-C₁₂-alkyl substituted with halogen, phenoxy, aryl, cyano, C₃-C₈-cycloalkyl, C₁-C₆-alkylsulfonyl, C₁-C₆-alkylthio, or C₁-C₆-alkoxy; R₁₄ and R'₁₄ are independently selected from hydrogen, aryl, C₁-C₁₂-alkyl and C₁-C₁₂-alkyl substituted with halogen, phenoxy, aryl, —CN, cycloalkyl, C₁-C₆-alkylsulfonyl, C₁-C₆-alkylthio, or C₁-C₆-alkoxy; X₃ is selected from —CO—, —COO—, —CONH—, or —SO₂—; C₃-C₈-cycloalkyl; C₁-C₆-alkanoyloxy; C₁-C₆-alkoxycarbonyl and —(O—C₂-C₄-alkylene)$_n$R₁₅; wherein R₁₅ is selected from hydrogen, C₁-C₆-alkoxy, halogen, hydroxy, cyano, C₁-C₆-alkanoyloxy, C₁-C₆-alkoxycarbonyl, aryl, and C₃-C₈-cycloalkyl; groups of the formula

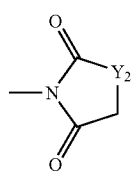

wherein $Y_2$ is —NH—, —N($C_1$-$C_{12}$-alkyl)-, —O—, —S—, and —$CH_2O$—; —OQ; —O-L-Q; —COY;

wherein Q, L, Y, and n are as previously defined;

The term "$C_1$-$C_6$-alkylene" refers to a straight or branched chain, divalent hydrocarbon radical containing one to six carbon atoms and optionally substituted with hydroxy, halogen, aryl, $C_1$-$C_6$-alkanoyloxy, or —OQ.

The term "halogen" means any of the following atoms: fluorine, chlorine, bromine, and iodine.

The terms "$C_1$-$C_6$-alkoxy", $C_1$-$C_6$-alkoxycarbonyl" and "$C_1$-$C_6$-alkanoyloxy" denote the radicals —O$C_1$-$C_6$-alkyl, —$CO_2C_1$-$C_6$-alkyl, and —O—CO$C_1$-$C_6$-alkyl, respectively, wherein the $C_1$-$C_6$-alkyl group is as defined above.

The term "$C_3$-$C_8$ alkenyl" denotes a straight or branched chain hydrocarbon radical that contains at least one carbon-carbon double bond and three to eight carbon atoms.

In the terms "arylsulfonyl", "arylthio", "aryloxy," and "aroyl" the aryl groups or aryl portions of the groups are selected from phenyl and naphthyl, and these may optionally be substituted with hydroxy, halogen, carboxy, $C_1$-$C_6$-alkyl, $C_1$-$C_6$-alkoxy, $C_1$-$C_6$-alkoxycarbonyl, —O-L-Q, and COY, wherein L, Q, and Y as are previously defined.

The term "carbamoyl" is used to represent the group having the formula: —CON($R_{16}$)$R_{17}$, wherein $R_{16}$ and $R_{17}$ are selected from hydrogen, $C_1$-$C_6$-alkyl, $C_3$-$C_8$-cycloalkyl, $C_3$-$C_8$-alkenyl, and aryl, or these are combined or make cyclic structures such as morpholines, thiomorpholines, piperazines and thiomorpholine-S,S-dioxides.

The term "$C_1$-$C_6$-alkylsulfonyl" is used to represent —$SO_2$—$C_1$-$C_6$-alkyl wherein the term "$C_1$-$C_6$-alkyl" is as previously defined.

References herein to groups or moieties having a stated range of carbon atoms, such as "$C_1$-$C_6$-alkyl," shall mean not only the $C_1$ group (methyl) and $C_6$ group (hexyl) end points, but also each of the corresponding individual $C_2$, $C_3$, $C_4$, and $C_5$ groups. In addition, it will be understood that each of the individual points within a stated range of carbon atoms may be further combined to describe subranges that are inherently within the stated overall range. For example, the term "$C_3$-$C_8$-cycloalkyl" includes not only the individual cyclic moieties $C_3$ through $C_8$, but also contemplates subranges such as "$C_4$-$C_6$-cycloalkyl" and alkyl substituted cycloalkyl.

The phrase "ethylenically unsaturated polymerizable group" shall mean a moiety having a C=C double bond that is reactive in a free radical polymerization. In some embodiments, the reactive double bond is activated by one of the double-bonded carbons being attached to an aryl group or an electron withdrawing group such as a carbonyl. Although aromatic and heteroaromatic rings are often drawn in this application and elsewhere in a way that depicts the aromatic pi cloud of electrons in such rings as alternating double bonds (for example, benzene is often drawn as a six membered ring containing three alternating double and single bonds) the skilled artisan will understand that such rings do not actually contain double bonds but instead contain an aromatic pi cloud of completely delocalized electrons and, as such, are unreactive to free radical polymerization. Accordingly, the term "ethylenically unsaturated polymerizable group" does not include aromatic pi clouds of electrons in aromatic or heteroaromatic ring, irrespective of whether such aromatic pi clouds of electrons are representing in any drawing as alternating double bonds.

Ultraviolet Light Absorbing Compositions

Typically, topical application of the UV absorbing polymers to skin sites is accomplished in association with a carrier, and particularly one in which the active ingredient is soluble per se or is effectively solubilized (e.g., as an emulsion, dispersion or microemulsion). Where employed, the carrier is inert in the sense of not bringing about a deactivation or oxidation of active ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. While the carrier for dermatological compositions can consist of a relatively simple solvent or dispersant such as water or ethanol, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of an active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermally, dermatologically, or pharmaceutically acceptable carriers.

Generally in the practice of methods of the invention, the composition is topically applied to skin areas in a predetermined or as-needed regimen typically at intervals by application of a lotion or the like.

EXAMPLES

Examples 1 through 58 are prophetic examples of some of the compounds that are within the present invention. These examples use Formulas Ia through Id to describe compounds by identifying the various groups in Formulas Ia through Id. Examples 1 through 18 identify compounds using Formula Ic. Examples 19 through 36 identify compounds using Formula Ia. For Examples 1 through 36, in cases where numbers are provided along with the identity of the X groups in the tables, those numbers indicate the position on the ring in the diagram of Formula Ia or Formula Ic, as applicable. Examples 37 through 58 identify compounds using Formula Ib and Id. These examples follow, with the formulas provided for reference, each at the beginning of group of examples to which they apply.

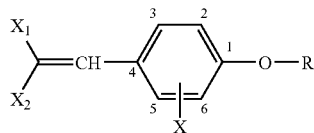

| Example Number | X | R | $X_1$ | $X_2$ |
|---|---|---|---|---|
| 1 | —H | —H | —CN | acetamido-methyl-propyl methacrylate |
| 2 | —H | —CH$_3$ | —CN | acetamido-methyl-propyl methacrylate |
| 3 | -2-OCH$_3$ | propyl methacrylate | —CN | —CN |
| 4 | -2-OCH$_3$ | isobutyl methacrylate | —CN | —C$_6$H$_5$ |
| 5 | -2-OCH$_3$ | isobutyl methacrylate | —CN | 2-ethylhexyl acetate |
| 6 | —H | isobutyl methacrylate | —CN | —CN |
| 7 | —H | isobutyl methacrylate | —CN | —C$_6$H$_5$ |
| 8 | —H | isobutyl methacrylate | —CN | 2-ethylhexyl acetate |
| 9 | —H | isobutyl methacrylate | —CO$_2$C$_2$H$_5$ | —CO$_2$C$_2$H$_5$ |

-continued

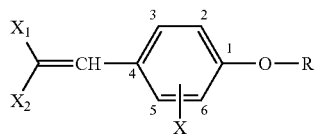

Ic

| Example Number | X | R | $X_1$ | $X_2$ |
|---|---|---|---|---|
| 10 | —H | —CH$_3$ | —CN | acetamido-NH(C$_2$H$_4$O)$_{6-10}$—(CH$_2$CHCH$_3$O)$_{6-10}$ methacrylate |
| 1 | —H | (CH$_2$CH$_2$O)$_{3-20}$ methacrylate | —CN | —CO$_2$CH$_3$ |
| 12 | -2-OCH$_3$ | —CH$_3$ | —CN | acetamido-isopropyl methacrylate |
| 13 | -2-OCH$_3$ | —CH$_3$ | —CN | acetamido-ethyl methacrylate |
| 14 | -2-OCH$_3$ | —CH$_3$ | —CN | acetamido-methyl-cyclohexyl-methyl methacrylate |
| 15 | -3-Br | isobutyl methacrylate | —CN | 2-ethylhexyl acetate |
| 16 | -3-OCH$_3$ | —CH$_2$C$_6$H$_5$ | acetamido-isopropyl methacrylate | acetamido-isopropyl methacrylate |
| 7 | —H | —CH$_2$C$_6$H$_5$ | —CN | acetamido-ethoxyethyl methacrylate |
| 18 | -3-OCH$_3$ | H | —CN | acetamido-isopropyl methacrylate |

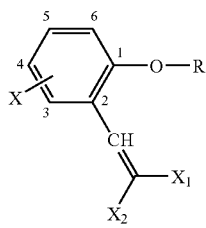

Ia

| Example Number | X | R | $X_1$ | $X_2$ |
|---|---|---|---|---|
| 19 | —H | —H | —CN | ![acetamido methyl methacrylate ester] |
| 20 | —H | —CH$_3$ | —CN | ![acetamido methyl methacrylate ester] |
| 21 | -4-OCH$_3$ | ![isobutyl methacrylate] | —CN | —CN |
| 22 | -4-OCH$_3$ | ![isobutyl methacrylate] | —CN | —C$_6$H$_5$ |
| 23 | -5-OCH$_3$ | ![isobutyl methacrylate] | —CN | ![2-ethylhexyl acetate] |
| 24 | —H | ![isobutyl methacrylate] | —CN | —CN |
| 25 | —H | ![isobutyl methacrylate trimer] | —CN | —C$_6$H$_5$ |
| 26 | —H | ![isobutyl methacrylate] | —CN | ![2-ethylhexyl acetate] |

-continued
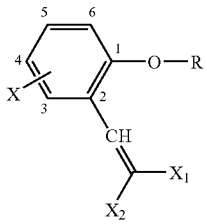
Ia
| Example Number | X | R | $X_1$ | $X_2$ |
|---|---|---|---|---|
| 27 | —H | 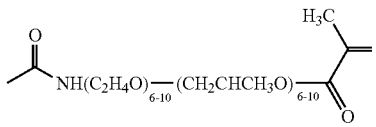 | —$CO_2C_2H_5$ | —$CO_2C_2H_5$ |
| 28 | —H | —$CH_3$ | —CN | 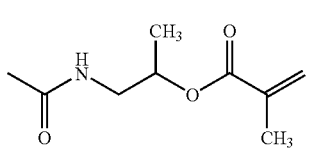 |
| 29 | —H | 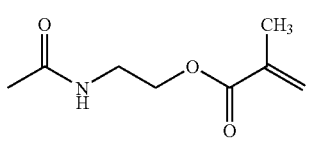 | —CN | —$CO_2CH_3$ |
| 30 | -4-OH | —$CH_3$ | —CN | 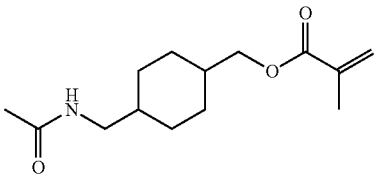 |
| 31 | -4-OH | —$CH_3$ | —CN | 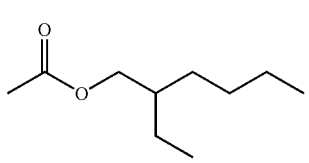 |
| 32 | -5-$OCH_3$ | —$CH_3$ | —CN | 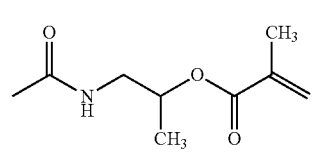 |
| 33 | -3-Br | 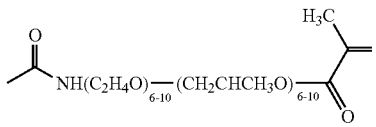 | —CN | 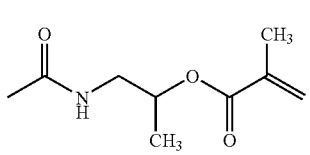 |
| 34 | -4-$OCH_3$ | —$CH_2C_6H_5$ | 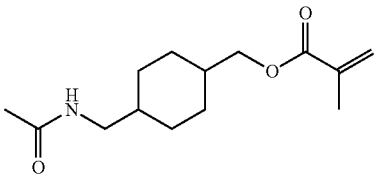 | 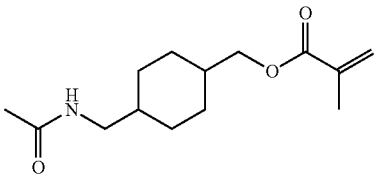 |

-continued
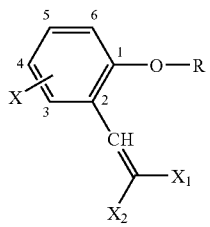
Ia
| Example Number | X | R | $X_1$ | $X_2$ |
|---|---|---|---|---|
| 35 | —H | —CH$_2$C$_6$H$_5$ | —CN | ![structure] |
| 36 | -5-OCH$_3$ | H | —CN | ![structure] |
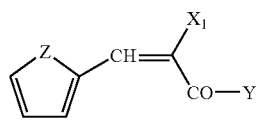
Z = O: Id
Z = S: Ib
| Example Number | $X_1$ | Z | Y |
|---|---|---|---|
| 37 | —CN | O | ![structure] |
| 38 | —CN | O | ![structure] |
| 39 | —CN | O | ![structure] |
| 40 | —CN | O | ![structure] |
| 41 | —C(O)CH$_3$ | O | ![structure] |

-continued

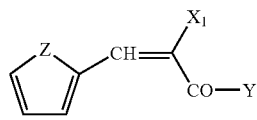

Z = O: Id
Z = S: Ib

| Example Number | X₁ | Z | Y |
|---|---|---|---|
| 42 | acetyl-phenyl (PhC(O)-) | O | -NH-CH(CH₃)-CH₂-O-C(O)-CH=CH₂ |
| 43 | 4-methyl-C₆H₄-CO₂CH₃ | O | -NH-CH₂CH₂-O-C(O)-C(CH₃)=CH₂ |
| 44 | —C(O)C(CH₃)₃ | O | -NH-CH₂-C(CH₃)₂-CH₂-O-C(O)-CH=CH₂ |
| 45 | PhC(O)- | O | -NH-CH(CH₃)-CH₂-O-C(O)-CH=CH₂ |
| 46 | —CN | O | -NH-CH₂-(cyclohexyl)-CH₂-O-C(O)-C(CH₃)=CH₂ |
| 47 | 2-ethylhexyl acetate | O | CH₃O-(C₂H₄O)₆₋₁₀-(CH(CH₃)CH₂O)₆₋₁₀-C(O)-CH=CH₂ |
| 48 | —CN | S | -NH-CH(CH₃)-CH₂-O-C(O)-CH=CH₂ |
| 49 | —CN | S | -NH-CH(CH₃)-CH₂-O-C(O)-CH=CH₂ |
| 50 | —CN | S | —NH—CH₂CH₂—OCOC(CH₃)=CH₂ |
| 51 | —CN | S | -NH-CH₂-(cyclohexyl)-CH₂-O-C(O)-C(CH₃)=CH₂ |
| 52 | —C(O)CH₃ | S | -NH-CH₂CH₂-O-C(O)-CH=CH₂ |

-continued
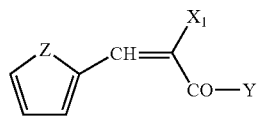
Z = O: Id
Z = S: Ib
| Example Number | X₁ | Z | Y |
|---|---|---|---|
| 53 | 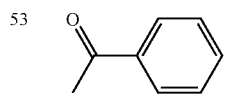 | S | 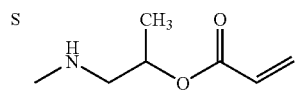 |
| 54 | 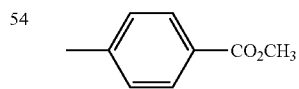 | S | 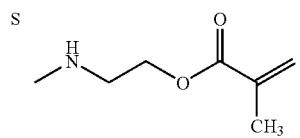 |
| 55 | —C(O)C(CH₃)₃ | S | 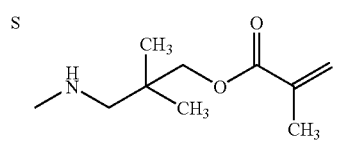 |
| 56 | 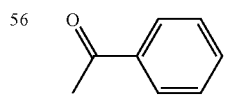 | S | 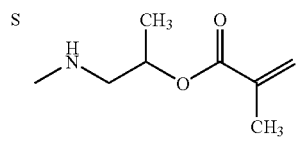 |
| 57 | —CN | S | 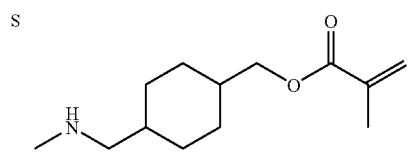 |
| 58 | 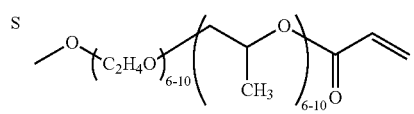 | S | 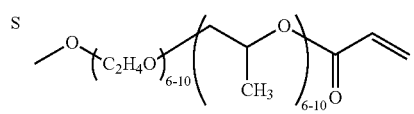 |

Examples 59 through 76 describe actual procedures that were performed in preparing some of the compounds of the present invention and their precursors. Each of Examples 59 through 76 includes a drawing to show the reaction and its product. Stereochemistry of the products of these reactions was not determined, so the diagrams in Examples 59 through 76 should not be interpreted as distinguishing the cis or trans stereoisomer.

Examples 77 through 90 describe examples of some of the procedures for preparing a polymer and polymerizing compounds. Examples 91 and 92 describe examples of some of the procedures for formulating the polymeric sunscreens.

Example 59

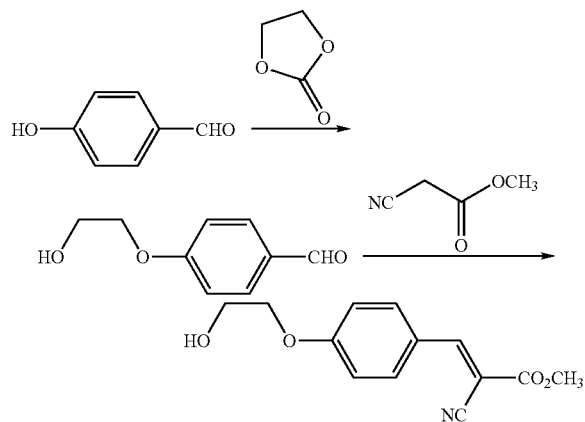

In a one liter three-neck round-bottom flask equipped with a reflux condenser, heating mantle, thermocouple and overhead stirrer were added 88 g (1.0 mol) of ethylene carbonate, 4 g of potassium iodide and 97.6 g (0.8 mol) of 4-hydroxybenzaldehyde. The above ingredients were heated to 160° for 1.25 hours. TLC in 1:1 cyclohexane: THF indicated little to no starting aldehyde present. The reaction mixture was cooled to about 70° C. and 80 g (0.8 moles) of methyl cyanoacetate was added along with 200 mL of B&J methanol and 6 drops of piperidine. The entire mixture was heated back to reflux for 2.5 hours. Heating was discontinued and the mixture allowed to cool overnight. The next day the mixture had thickened, so 300 mL of 75:25 blend of methanol:water (v/v) was added to the reaction and the mixture was heated back to 36°. Heating was then discontinued and the slurry was cooled to room temperature. The mixture was then filtered and washed with a 75:25 blend of methanol:water (v/v). Product (mp 125-127°) was produced at a yield of 53 percent and the 'HNMR spectra supported the structure.

Example 60

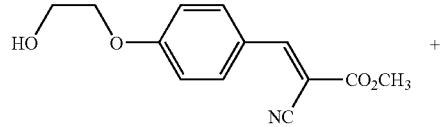

+

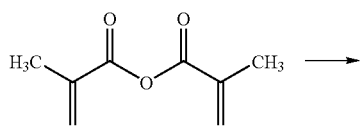

-continued

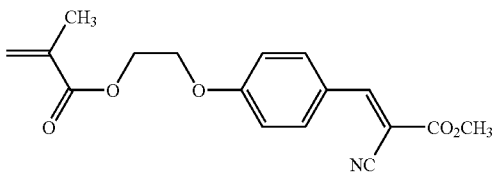

In a round-bottom flask equipped with mechanical stirring 57.5 g of the intermediate from Example 59 and 275 mL of DMF were stirred to a solution at room temp. To the same flask 43.4 mL (0.33 mol) of triethylamine, 0.43 g of hydroquinone and 0.43 g of 4-N,N-dimethylaminopyridine were also added. Then, 48.8 mL (0.33 mol) of methacrylic anhydride were added slowly at 20-30° and the resulting solution was stirred for 1-2 hours. TLC in 50/50 cyclohexane/THF indicated little to no starting material present. The reaction mixture was drowned onto 500 mL of deionized water and 500 g of ice. The mixture was allowed to sit overnight with no stirring. The next day the solid was filtered and washed with 1-liter of deionized water. After air drying the solid was slurried in 200 mL of isopropanol (B&J) for about 2 hours. After stirring the slurry was filtered, and washed then rinsed with a total of 100 mL of isopropanol. A pale yellow solid (57.9 g, 72.5%) was isolated with a melting point of 68 to 73°. The H[1]NMR spectrum supported the structure.

Example 61

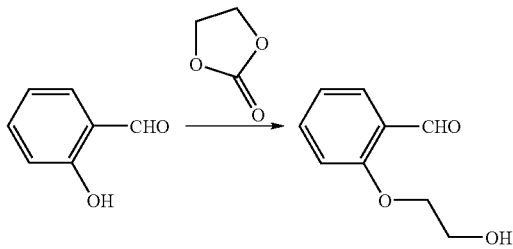

A mixture of 202 g (2.3 mol) of ethylene carbonate, 244 g (2.0 mol) of 2-hydroxybenzaldehyde, and 4 g of potassium iodide was heated to 145° C. for 18 hr. TLC in 1:1 cyclohexane:THF indicated little to no starting material present. The entire reaction mixture was distilled under vacuum using a 6 inch Vigreaux column. The fraction boiling at 137-141° C. at 0.5 mm, represented a yield of 159 g (48% of theory) was collected. It analyzed by gc at 98.7 area %.

Example 62

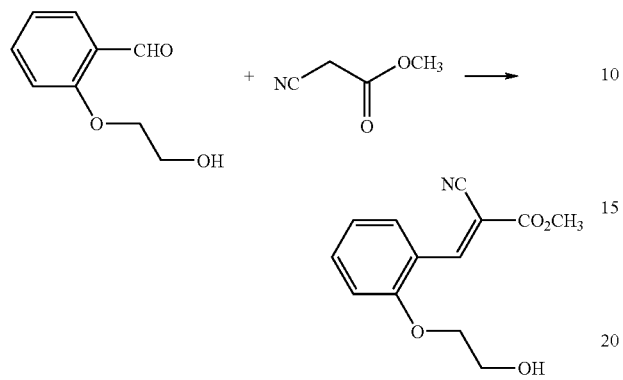

In a round-bottom flask equipped with mechanical stirring, heating mantle and reflux condenser were added 16.7 g of the aldehyde from Example 61 (0.1 mol), 10.5 g of methyl cyanoacetate (0.105 mol), 75 ml of methanol, and 0.5 g of piperidine acetate. The solution was heated at reflux for 4 hr. TLC in 1 to 1 cyclohexane/THF indicated little to no starting material. The solution was cooled to room temperature and 150 mL of deionized water was added to the reaction flask while stirring. The solids that formed were filtered and rinsed with 100 mL of deionized water and dried. The bright yellow solid was recrystallized from 90 mL of toluene to give 14.33 g (58 %) of a light yellow solid with a melting point of 97 to 99°. The $H^1$NMR spectrum supported the structure.

Example 63

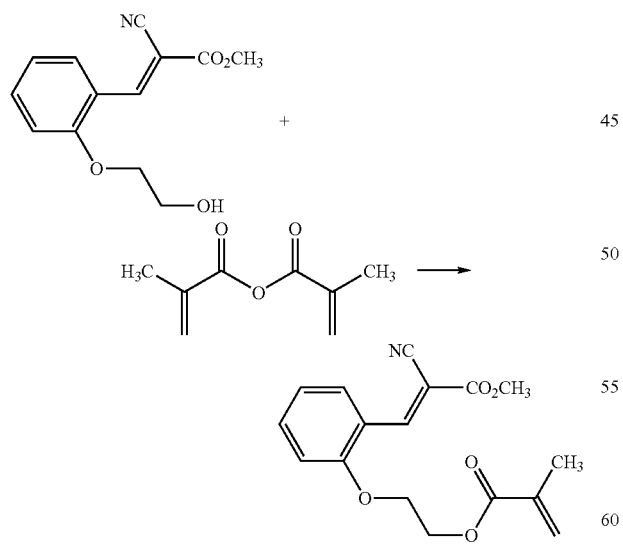

A solution of 14.33 g (0.058 mol) of the intermediate from Example 62, 67.5 mL of DMF, 10.8 mL (0.081 mol) of triethylamine, 0.108 g of hydroquinone, and 0.108 g of 4-N, N-dimethylaminopyridine was treated dropwise with 12.15 mL (0.081 mol) of methacrylic anhydride, controlling the exotherm at 20-30° C. The reaction was stirred for three hours. TLC in 70/30 heptane/ethyl acetate indicated little to no starting material. The reaction was poured onto about 210 mL of deionized water and 50 g of ice. The product was extracted with 150 mL of ethyl acetate and the resulting solution was washed three times with 250 mL of deionized water The organic layer was dried (magnesium sulfate) and the upper layer evaporated without heat. The yellow waxy solid, 18.42 g, (100.7%) was re-slurried in 60 mL of isopropanol, to give a light yellow solid, 12.43 g (68%), mp 58-60° C. $H^1$NMR supported it's structure.

Example 64

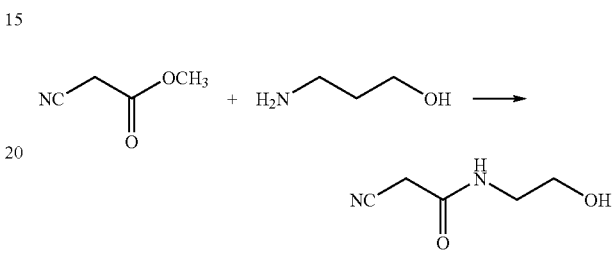

Methyl cyanoacetate (123 g, 1.25 mol) was heated to approx. 70° C. and a dropwise addition of ethanolamine (74 ml, 1.25 moles) was begun. The amine was added slowly at first to keep the accompanying exotherm below 80° C. When the exotherm subsided, the ethanolamine addition rate was increased and the pot temperature was increased to 85° C. Low boilers formed during the reaction were removed via the Dean Stark trap. When the addition was complete, the reaction temperature was increased to 95° C. where it was held until the take off of low boilers had ceased. Meanwhile, ethyl acetate (approx. 400 ml) and denatured ethanol (approx. 50 ml) were charged to a 2 L round bottom flask, and the resulting solution was cooled with stirring in an ice/water bath. After the generation of low boiler ceased, the reaction mixture was allowed to cool to 75-80° C. and was then poured slowly into the cold ethyl acetate/ethanol solution containing some seed crystals. The resulting slurry was cooled to 10° C. and filtered to collect the solid product which was washed with cold ethyl acetate then with heptane and air-dried. The yield was 124 g (96%). It melted at 61-63° C.

Example 65

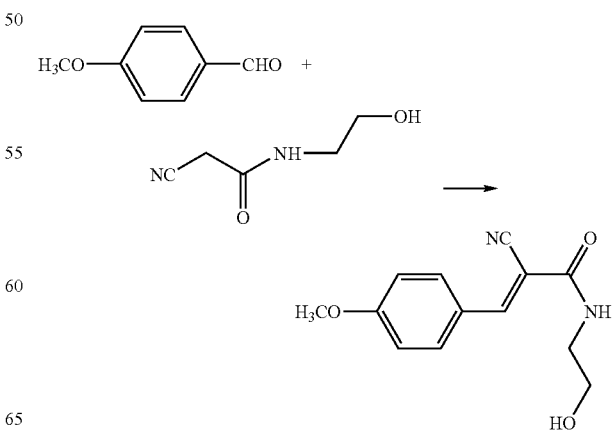

A solution of 100 mL of toluene, 13.6 g (0.1 mole) of p-methoxybenzaldehyde, 12.8 g (0.1 moles) 2-cyano-N-(2-hydroxyethyl)acetamide (from Example 64), and 0.2 g piperidine acetate was refluxed until no more water was removed to a Dean Stark trap. TLC in 70/30 (ethyl acetate/heptane) indicated little to no starting material A solid precipitated during cooling. The resulting slurry was cooled to room temperature, filtered, and the solids were washed with toluene and dried to yield 23.2 g (94%), of a white solid, mp 123-125° C. H$^1$NMR spectra supported the structure.

Example 66

A solution of 24.6 g of the intermediate from Example 65 (0.1 mol), 150 mL of DMF, 20 mL (0.15 mol) of triethylamine, 0.2 g of hydroquinone, and 0.2 g of 4-N,N-dimethylaminopyridine was treated dropwise with 22.5 mL (0.15 mol) of methacrylic anhydride, controlling the exotherm at 20-30° C. The reaction was stirred for one hour. TLC in (80/20) heptane/ethyl acetate indicated little to no starting material remaining. The reaction mixture was poured onto 250 mL of deionized water and 250 g ice. The entire mixture sat overnight at room temperature without stirring. The next day the solids were filtered and washed twice with 250 mL of deionized water. The off-white solid was reslurried in 85 mL of isopropanol to give 20.6 g (66%) of a pale yellow solid, mp 97-100°. H$^1$NMR spectra supported the structure.

Example 67

A solution of 100 mL of toluene, 13.6 g (0.1 moles) of o-anisaldehyde, 12.8 g (0.1 moles) of the intermediate from Example 64, and 0.2 g piperidine acetate was refluxed until no more water was removed to a Dean Stark trap. TLC in 70/30 (ethyl acetate/heptane) indicated little or no starting material. A solid precipitated during cooling to room temperature. The solids were filtered and washed with toluene to give 21.0 g (85%) of white solid whose H$^1$NMR spectra supported the structure. Reslurry from 3 parts of isopropanol gave a recovery of 77%, mp 130-135° C.

Example 68

A solution of 9.70 g (0.04 mol) of the intermediate from Example 67, 59 mL of DMF, 7.8 mL (0.15 moles) of triethylamine, 0.1 g of hydroquinone, and 0.1 g of 4-N,N-dimethylaminopyridine was treated dropwise with 8.8 mL (0.15 mol) of methacrylic anhydride allowing the temperature to rise to 30° C. After one hour TLC in 50/50 cyclohexane/THF indicated little to no starting material present. The reaction mixture was poured onto 100 mL of deionized water and 100 g ice and the product was extracted with 100 mL of ethyl acetate. The organic layer was washed twice with 200 mL of deionized water, dried (magnesium sulfate), and evaporated without heat to give 13.6 g of a white solid which was reslurried in 30 mL of isopropanol to give 6.6 g (52%) of a fine white solid, mp 68 to 72°. H¹NMR spectra of the product supported the structure.

Example 69

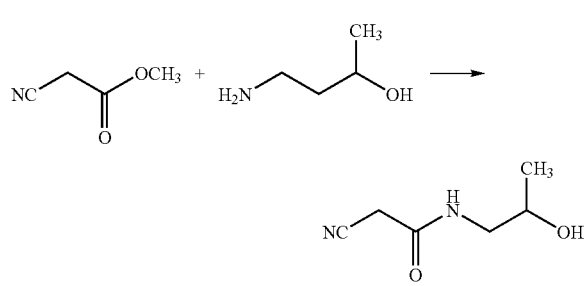

Methyl cyanoacetate (132.3 mL, 148.6 g, 1.5 m) was charged to a 500 mL four-neck round bottom flask equipped with a magnetic stirrer, heating mantle and a Dean Stark trap. The methyl cyanoacetate was heated to approx. 80° C. with stirring under a light nitrogen purge. 1-Amino-2-propanol (113 g, 1.5 m) was added drop wise, slowly at first, then more rapidly as the addition progressed. In the course of the addition, the temperature was increased in five degree increments to 90-95° C. Low boiling products of the reaction were removed continually via the Dean Stark trap. When the addition of the amine was complete the reaction mixture was stirred for approximately 30 min. at 105-110° C. to ensure removal of low boilers. After cooling to about 75° C., the viscous liquid product was bottled. The yield was essentially quantitative. The material eventually crystallized on standing.

Example 70

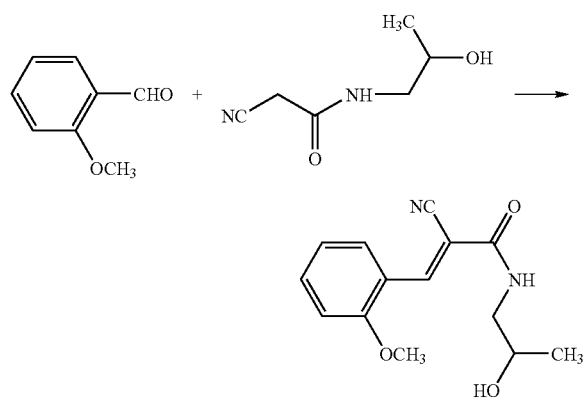

A solution of 25.6 g of the compound from Example 69 (0.18 moles), 27.2 g of o-anisaldehyde (0.2 moles), 0.4 g of piperidine acetate and 200 mL of toluene was refluxed, removing water to a Dean Stark trap. After 4 hr, tlc indicated that the reaction was nearly complete. The solution was cooled, filtered, and the product was washed with toluene to give 35.4 g (76%) of a pale yellow solid, mp 127-131°, whose H¹NMR spectrum supported its structure.

Example 71

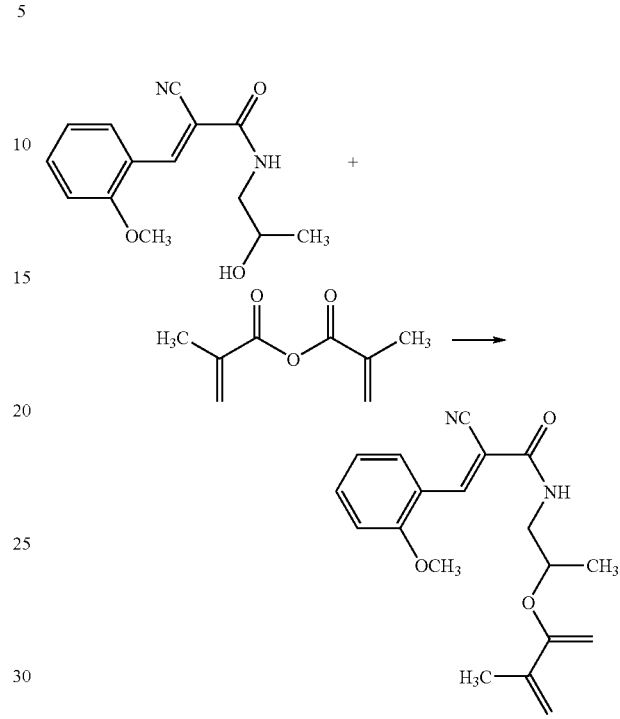

A solution of 34.6 g of the compound from Example 70 (0.13 moles), 166 mL of DMF, 26.6 mL of triethylamine (0.2 moles), and 0.27 g of hydroquinone was treated dropwise at 20-30° C. with 30 mL of methacrylic anhydride. The reaction was slightly exothermic. After a few hours tlc analysis indicated no starting material was present. The solution was drowned onto 300 g of ice and 300 g of water and the resulting oil was extracted with 300 mL of ethyl acetate. The ethyl acetate solution was washed 3 times with 250 mL of water, and dried (MgSO$_4$). The MgSO$_4$ was removed by filtration and the ethyl acetate was removed at room temperature in a roto-evaporator. A thick yellow liquid (53.3 g) was obtained. Analysis by nmr indicated that the product was contaminated with about 10% ethyl acetate. Analysis by liquid chromatography indicated a purity of 91% on a solvent-free basis.

Example 72

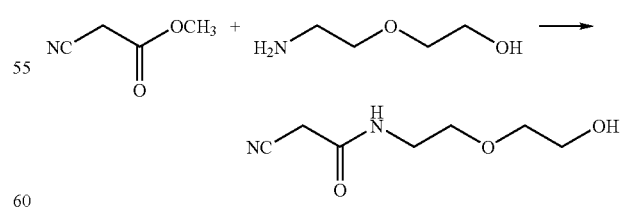

Methyl cyanoacetate (123.8 g, 1.25 moles) was heated to 80° and a slow addition of 131.2 g (1.25 moles) of 2-(2-amonoethoxy)ethanol was begun. Methanol was removed by means of a distillation head as it formed. During the addition the pot temperature was increased to 95° C. When the addition was complete the pot temperature was raised to 115° C.

and when methanol evolution stopped, the reaction product was cooled to room temperature and was bottled. The theoretical amount of methanol was evolved during the process. The product (216 g, 99% of theory) was a light brown liquid whose H¹NMR supported its structure.

Example 73

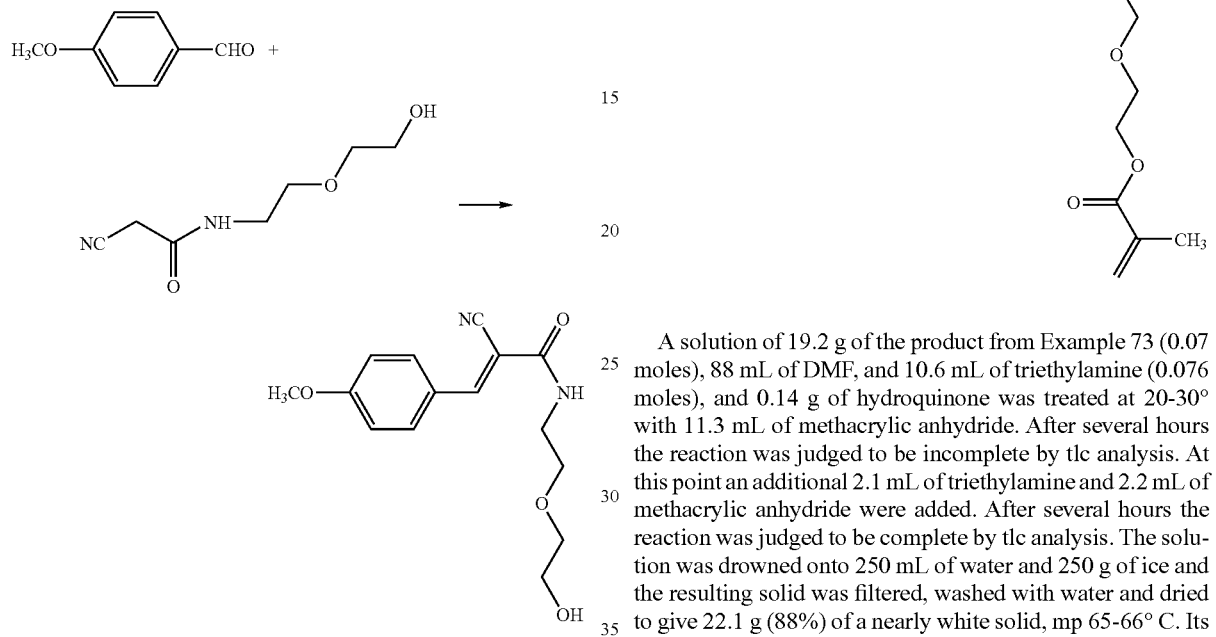

A solution of 20 g of the compound from Example 72 (0.12 moles), 13.6 g of p-methoxybenzaldehyde (0.1 moles), 0.3 g of piperidine acetate and 100 mL of toluene was refluxed, removing water to a Dean Stark trap. After 4 hr, tlc indicated that the reaction was complete. The solution was cooled and the thick slurry was thinned with 50 mL of toluene. The product was collected by filtration and the solids were washed with toluene to give 27.2 g of a pale yellow solid, mp 90-93° C. The product was reslurried in water to give 19.2 g (66%) of nearly white material, mp 98-100° C. The H¹NMR spectrum of this product supported its structure.

Example 74

A solution of 19.2 g of the product from Example 73 (0.07 moles), 88 mL of DMF, and 10.6 mL of triethylamine (0.076 moles), and 0.14 g of hydroquinone was treated at 20-30° with 11.3 mL of methacrylic anhydride. After several hours the reaction was judged to be incomplete by tlc analysis. At this point an additional 2.1 mL of triethylamine and 2.2 mL of methacrylic anhydride were added. After several hours the reaction was judged to be complete by tlc analysis. The solution was drowned onto 250 mL of water and 250 g of ice and the resulting solid was filtered, washed with water and dried to give 22.1 g (88%) of a nearly white solid, mp 65-66° C. Its H¹NMR spectrum supported its structure.

Example 75

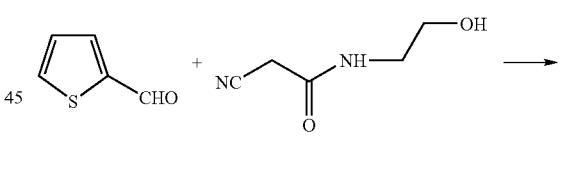

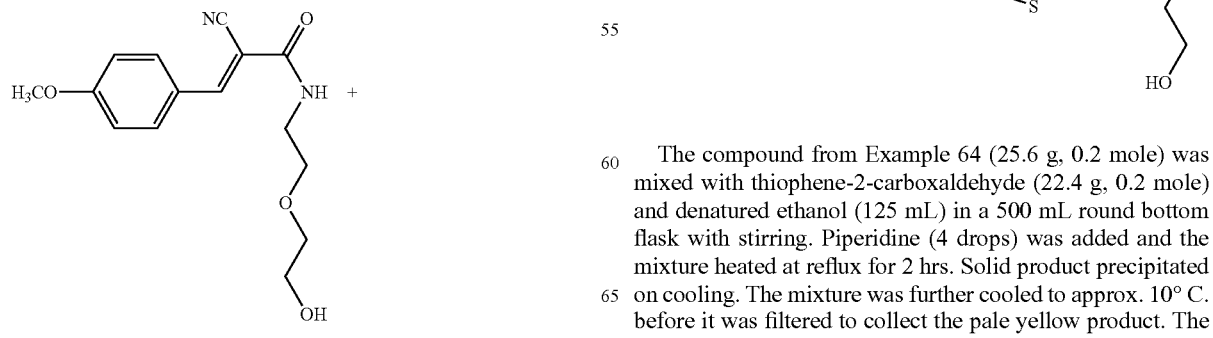

The compound from Example 64 (25.6 g, 0.2 mole) was mixed with thiophene-2-carboxaldehyde (22.4 g, 0.2 mole) and denatured ethanol (125 mL) in a 500 mL round bottom flask with stirring. Piperidine (4 drops) was added and the mixture heated at reflux for 2 hrs. Solid product precipitated on cooling. The mixture was further cooled to approx. 10° C. before it was filtered to collect the pale yellow product. The solid was washed with cold methanol and air dried. The yield

Example 76

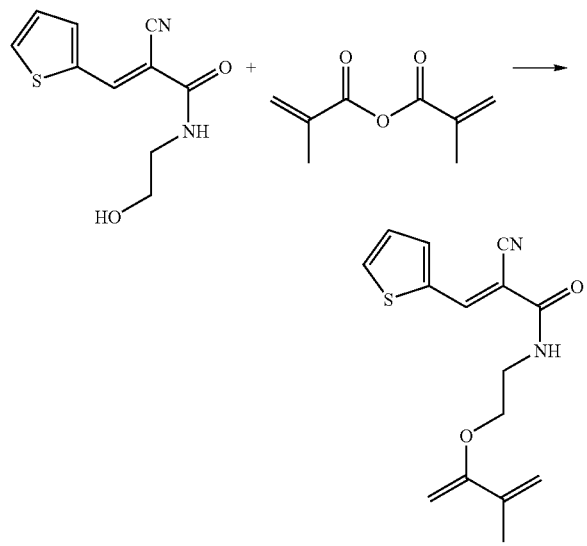

The compound from Example 75 (11.1 g, 50 mmoles), 20 mL of DMF, 6.1 g of triethylamine (60 mmoles) was stirred to a solution and 9.25 g of methacrylic anhydride (60 mmoles) was added dropwise below 30° C. After stirring at 20-30° C. for 3 hr, solids precipitated to produce a thick slurry. Analysis by tlc indicated a complete reaction. The slurry was diluted with 20 mL of methanol and the product was recovered by filtration, washed with methanol, and the damp solid was reslurried from isopropanol to give 8.9 g (69%) of a light colored solid, mp 130-132° C. Its H¹NMR spectrum supported its structure.

Example 77

Homopolymer from Monomer of Example 71

A solution of 3 g of chromophoric monomer from Example 71, 20 mL of DMF and 0.25 g of benzoyl peroxide was heated from 3 hr at 90-95° C. The resulting solution was cooled to 70° C. and drowned into 150 mL of water. The product polymer was filtered, washed with water and dried to give 2.7 g of light tan solid whose molecular weight by GPC ($M_w$) was 5100.

Example 78

Copolymer from Monomer of Example 71 and Methyl Methacrylate

The above procedure was repeated exactly, except that the monomer composition was changed to 1.5 g of chromophoric monomer from Example 71 and 1.5 g of methyl methacrylate. The product weighed 2.7 g, and its molecular weight by GPC ($M_w$) was 46675.

Example 79

Copolymer from Monomer of Example 60 and Methyl Methacrylate

A solution of 4 g of the chromophoric monomer from Example 60, 5 g of methyl methacrylate, 20 mL of n-butyl acetate and 0.4 mL of t-butylperoxy isopropyl carbonate, 75% in mineral spirits, was heated at 115-120° C. for 3 hr. Solids precipitated during the hold time. The slurry was cooled to 80° C. and diluted with 60 mL of heptane. The slurry was cooled to room temperature and the product was collected by filtration and washed with heptane and air dried. A lightly-colored polymer (10 g), molecular weight by GPC ($M_w$)=46675, was obtained.

Example 80

Copolymer from Monomer of Example 63 and Methyl Methacrylate

A solution of 3 g of the chromophoric monomer from Example 63, 3 g of methyl methacrylate, 25 mL of n-butyl acetate and 0.4 mL of t-butylperoxy isopropyl carbonate, 75% in mineral spirits, was heated at 115-120° C. for 3 hr. Solids precipitated during the hold time. The slurry was cooled to 80° C. and drowned into 300 mL of heptane. The slurry was cooled to room temperature and the product was collected by filtration and washed with heptane and air dried. A lightly-colored polymer (4.7 g), molecular weight by GPC ($M_w$)=15622, was obtained.

Example 81

Homopolymer from Monomer of Example 66

A solution of 3 g of chromophoric monomer from Example 65, 20 mL of DMF and 0.25 g of benzoyl peroxide was heated for 3 hr at 90-95° C. The resulting solution was cooled to 70° and drowned into 200 mL of water. The product polymer was filtered, washed with water and dried to give 2.87 g of light tan solid whose molecular weight by GPC ($M_w$) was 8089. Its lambda max (acetonitrile) was 332 nm.

Example 82

Copolymer from Monomer of Example 66 and Methyl Methacrylate

A solution of 1.5 g of chromophoric monomer from Example 65, 1.5 g of methyl methacrylate, 20 mL of DMF and 0.25 g of benzoyl peroxide was heated for 3 hr at 90-95° C. The resulting solution was cooled to 70° and drowned into 200 mL of water. The product polymer was filtered, washed with water and dried to give 2.71 g of light tan solid whose molecular weight by GPC ($M_w$) was 7971. Its lambda max (acetonitrile) was 332 nm.

Example 83

Copolymer from Monomer of Example 68 and Methyl Methacrylate

A solution of 1.5 g of the chromophoric monomer from Example 68, 1.5 g of methyl methacrylate, 20 mL of n-butyl acetate and 0.2 mL of t-butylperoxy isopropyl carbonate, 75% in mineral spirits, was heated at 120-125° C. for 3 hr. Solids precipitated during the hold time. The slurry was cooled to 80° C. and diluted with 60 mL of heptane. The slurry was cooled to room temperature and the product was collected by filtration and washed with heptane and air dried. A lightly-colored polymer (1.8 g), molecular weight by GPC ($M_w$)=9964, was obtained. Its UV spectra in acetonitrile showed two absorption peaks, one at 290 nm and one at 360 nm. The 290 nm peak was about 25% stronger than the 360 nm peak.

Example 84

Copolymer from Monomer of Example 60, Example 63, and Methyl Methacrylate

A solution of 0.4 of the chromophoric monomer from Example 60, 3.6 g of the chromophoric monomer from Example 63, 4 g of methyl methacrylate, and 25 mL of n-butyl acetate was warmed to 100° C. and 0.2 mL of t-butylperoxy isopropyl carbonate, 75% in mineral spirits, was added all at once via syringe. The solution was heated at 110-115° C. for 3 hr. Solids precipitated during the hold time. The slurry was cooled to 80° C. and drowned into 200 mL of heptane. The resulting slurry was cooled to room temperature and the product was collected by filtration and washed with heptane and air dried. A lightly-colored polymer (6.8 g), molecular weight by GPC ($M_w$)=27106, was obtained. Its UV spectra in acetonitrile showed two absorption peaks, one at 290 nm and one at 360 nm. The peaks were approximately equal in strength.

Example 85

Copolymer from Monomer of Example 60, Example 63, Methacrylic Acid, and Methyl Methacrylate as a Latex Emulsion To a 250 ml resin kettle equipped with a condenser, nitrogen purge, and a subsurface feed tube was added 40 g of water, 0.2 g of Sodium Dodecyl Sulfate surfactant and 0.6 g of Eumulgin B2PH surfactant. A nitrogen purge was begun and the mixture was stirred at 200 rpm while heating the contents to 82° C. A warm (35° C.) solution of 1 g of the chromophoric monomeric from Example 60, 19 g of the chromophoric monomeric from Example 63, and 10 g of methyl methacrylate was prepared. In a separate flask were mixed 0.1 g of Sodium Dodecyl Sulfate, 0.2 g of Eumulgin B2PH surfactants and 25 g of water. A monomer pre-emulsion was prepared by adding to this water surfactant mixture, the above warm solution of monomers and 3 g of Methacrylic acid. The mixture was stirred at room temperature for 30 minutes to obtain a stable milky looking pre-emulsion.

Four (4) grams of above pre-emulsion was charged to the reactor at about 78° C. Then 0.02 g of ammonium persulfate was mixed in 1 g of water and charged to the reactor mixture, held at 78° C. After 10 minutes, the remaining pre-emulsion was fed manually with help of a disposable pipette over a period of 50 minutes to the reactor. Simultaneously, an initiator feed composed of 20 g of water and 0.1 g of ammonium persulfate was also fed to the reactor over the time period of 60 min. After the feeds ended, the reactor was held at 78-82° C. for additional 60 minutes. Then a reductant solution consisting of 2.0 g water and 0.01 g of ascorbic acid was added to the reactor. A solution of 5 g water and 1 g of 30% hydrogen peroxide was then fed to the reactor over 60 minutes. The reaction mixture was cooled to room temperature. The latex was filtered through a 100 mesh wire screen. The particle size was measured using Microtrac UPA Particle Size Analyzer— laser light-scattering device (180 degree backscattering). For this particle size measurement the sample was diluted approximately 1:50 in water. The resulting latex (115 g) had the following properties. Solids: 21.8%, Viscosity (Sp2@60 rpm): 7 cps, Average Particle size: 99 nm. A dried down sample had a UV spectrum nearly identical to that of Example 83.

Example 86

Copolymer from Monomer of Example 68, Methacrylic Acid, and n-Butyl Acrylate as a Latex Emulsion To a 250 ml resin kettle equipped with a condenser, nitrogen purge, and a subsurface feed tube was added 65 g of water, 0.3 g of Sodium Dodecyl Sulfate surfactant and 1.0 g of Eumulgin B2PH surfactant. A nitrogen purge was begun and the mixture was stirred at 200 rpm while heating the contents to 82° C. At 75° C., 28 g of the chromophoric monomer from Example 69 was added slowly to the reactor at such a rate to make sure that monomer melts in solution and does not separate out as powder. The reactor contents were mixed for additional 15 minutes at 75-78° C. followed by addition of 10.0 g of n-butyl acrylate and 2.0 g of methacrylic acid to the reactor. The reaction mixture was bulk polymerized at 75-78° C. by adding initiator solution over 100 minutes. The initiator solution consisted of 0.25 g of ammonium persulfate and 20 g of water. After the initiator feed was over, the reactor contents were held at 75-78° C. for additional hr. The reaction mixture was then cooled to room temperature. The latex was filtered through a 100 mesh wire screen to remove solids. The weight of the latex emulsion was 103 g and weight of the solids was 12.7 g. Analysis of the collected solids did not indicate it to be unreacted UV monomer. The particle size of latex emulsion was measured using Microtrac UPA Particle Size Analyzer—laser light-scattering device (180 degree backscattering). For this particle size measurement the sample was diluted approximately 1:50 in water. The resulting latex (103 g) had the following properties. Solids: 18.8%, Viscosity (Sp2@60 rpm): 25 cps, average particle size: 99 nm. The UV spectrum in DMF showed two absorption peaks, one at 290 nm and one at 360 nm. The 290 nm peak was about 25% stronger than the 360 nm peak.

Example 87

Copolymer from Monomer of Example 68, and Methacrylic Acid

A solution of 7 g of the chromophoric monomer of Example 68, 3 g of methacrylic acid, 0.2 g of benzoyl peroxide, 25 mL of n-butyl acetate, and 0.5 g of isooctyl-3-mercapto propionate was heated for 3 hr at 80-85° C. Solids precipitated during the hold time. The resulting slurry was cooled to room temperature and was filtered. The product was washed with n-butyl acetate and dried in a 60° C. vacuum oven to give 8.7 g of nearly white product. The molecular weight by GPC ($M_w$) was 40628, and the UV spectra in acetonitrile showed two absorption peaks, one at 290 nm and one at 360 nm. The 290 nm peak was about 25% stronger than the 360 nm peak.

Example 88

Copolymer from Monomer of Example 60, Example 63, and Methacrylic Acid

A solution of 0.5 g of the chromophoric monomer of Example 60, 4.5 g of the chromophoric monomer of Example 63, 5 g of methacrylic acid, 25 mL of n-butyl acetate, and 0.2 mL of t-butylperoxy isopropyl carbonate (75% in mineral spirits) was heated for 3 hr at 100-105° C. Solids precipitated during the hold time. The resulting slurry was cooled to room temperature and was filtered. The product was washed with n-butyl acetate and dried in a 60° vacuum oven to give 8.7 g of nearly white product. The molecular weight by GPC ($M_w$) was 47213, and the UV spectra in acetonitrile showed two absorption peaks, one at 290 nm and one at 360 nm. The peaks were approximately equal in strength.

Example 89

Copolymer from Monomer of Example 76 and Methacrylic Acid

A solution of 14 g of the chromophoric monomer of Example 76, 6 g of methacrylic acid, 80 mL of n-butyl acetate, and 0.8 g of benzoyl peroxide and 0.25 mL of isooctyl-3-mercapto propionate was heated for 3 hr at 80-85° C. Solids precipitated during the hold time. The resulting slurry was cooled to room temperature and was filtered. The product was washed with n-butyl acetate and dried in a 60° C. vacuum oven to give 12.2 g of nearly white product. The molecular weight by GPC ($M_w$) was 387668, and the UV spectra in DMF showed two absorption peaks, on at lambda max of 290 mn and the other at lambda max of 335 nm. The peak at 335 nm was approximately 2.5 times stronger than the one at 290 nm.

Example 90

Ultra Violet Light Absorbing Composition of Polymer from Example 68

A 10 weight percent solution of the polymer from Example 68 in Poyethylene Glycol-200 was prepared with gentle heating. The solution was cooled to room temperature. A portion (5 g) was mixed with 1.74 g of Dow Corning 3225C Silicone Oil and 3.26 g of Dow Corning 556 Silicon Oil and the mixture was warmed to about 50 o followed by homogenization at high speed for about 5 minutes. The stable emulsion exhibited the expected UV spectrum on an Optometrics SPF 290 Sunscreen Analyzer. See FIG. 1.

Example 91

Ultra Violet Light Absorbing Composition of Latex from Example 85

Figure 2:
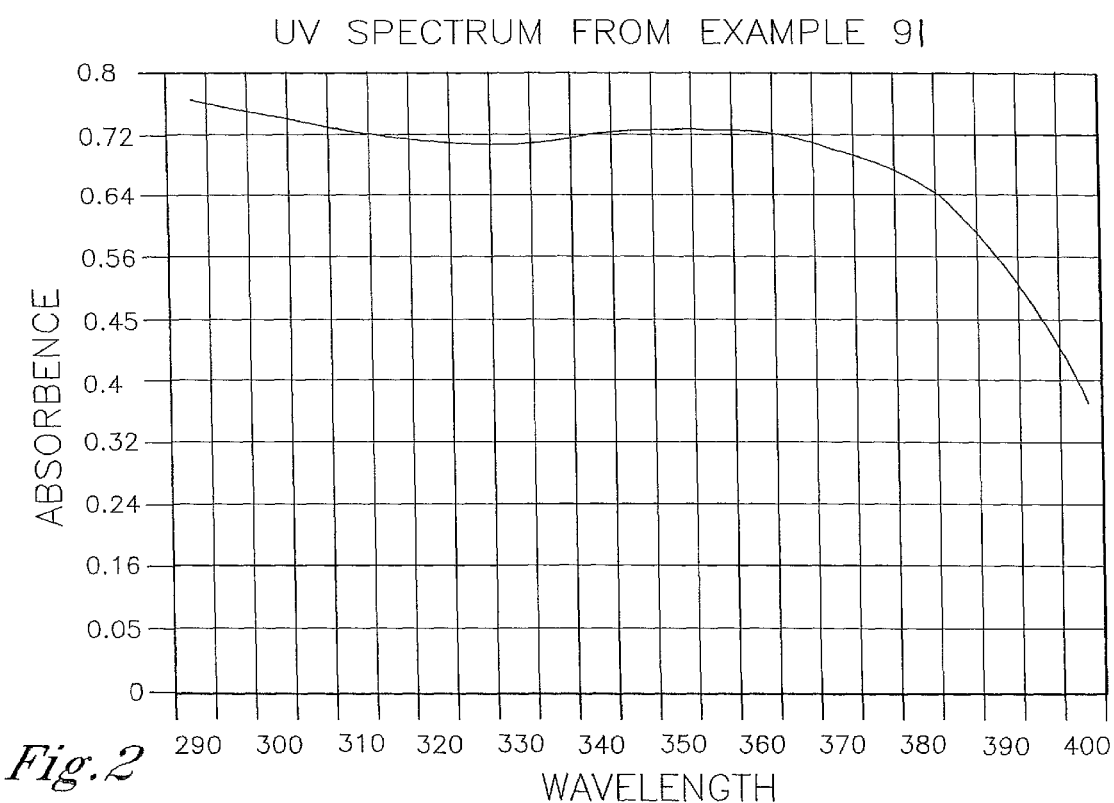
FIG. 2 shows the UV Spectrum of another Ultraviolet light absorbing composition according to the present invention.

A solution of 3.7 g of Mineral Oil, 0.6 g of Cetomacrogol BP 1000, 0.35 g of Promulen G, and 0.35 g of Cetyl Alcohol was mixed with 5 g of the Latex from Example 84. The mixture was homogenized at 70° C. at high speed for about 5 minutes. The stable emulsion exhibited the expected UV spectrum on an Optometrics SPF 290 Sunscreen Analyzer. See FIG. 2.

Example 93

Ultra Violet Light Absorbing Composition of Polymer from Example 87

Figure 3:
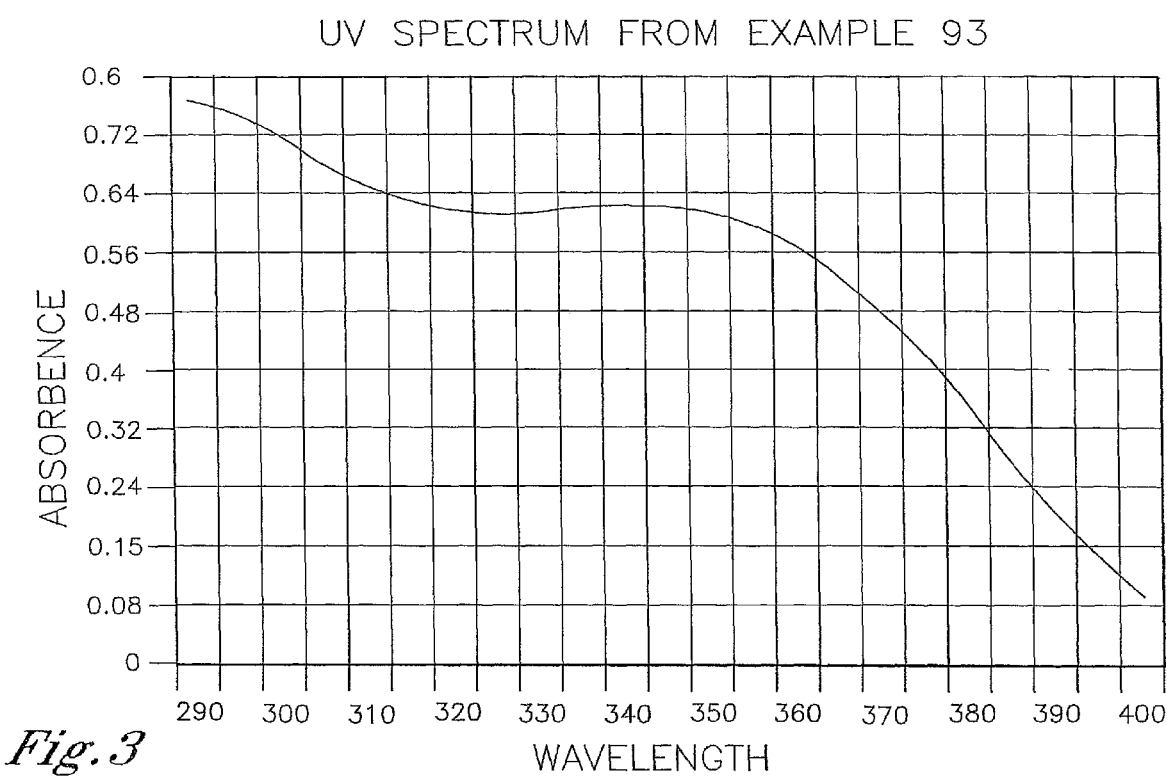
FIG. 3 shows the UV Spectrum of yet another Ultraviolet light absorbing composition according to the present invention.

A solution of 3 g of the polymer from Example 87, 2 g of triethanolamine, and 25 g of water was prepared by gently heating on a hot plate. The solution was cooled to room temperature. A solution of 3.7 g of mineral oil, 0.6 g of Cetomacrogol BP 1000, 0.35 g of Promulen G, and 0.35 g of Cetyl Alcohol was homogenized with 5 g of the aqueous solution of the Example 87 polymer. The homogenization was carried out at 70° at high speed for about 5 minutes. The milky emulsion was cooled to room temperature. It exhibited the expected UV spectrum on an Optometrics SPF 290 Sunscreen Analyzer. See FIG. 3.

The invention has been described in detail with particular reference to certain embodiments thereof, but it will be understood that variations and modifications can be effected within the spirit and scope of the invention.

We claim:
1. A polymeric UV absorbing composition, comprising:
a) a UV absorbing polymer comprising:
i) at least one residue of a chromophoric monomer structure depicted by Ia or Ib below or a combination thereof:

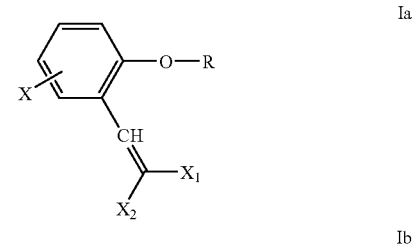

wherein X is hydrogen or one or two groups selected from the group consisting of hydroxy, $C_1$-$C_6$-alkyl, halogen, and —OR';

$X_1$ and $X_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;

R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$-alkenyl, —(CHR$_1$CHR$_2$O—)$_n$—R$_3$, and -L-Q;

wherein $R_1$ and $R_2$ are independently selected from the group consisting of hydrogen and $C_1$-$C_6$-alkyl;

$R_3$ is selected from the group consisting of hydrogen, $C_1$-$C_6$-alkyl, $C_1$-$C_6$-alkanoyl, aroyl, and aryl;

L is a divalent organic radical selected from the group consisting of $C_1$-$C_6$-alkylene-O—, $C_1$-$C_6$-alkylene-N(R$_1$)—, arylene-$C_1$-$C_6$-alkylene-O—, arylene-$C_1$-$C_6$-alkylene-(NR$_1$)—, arylene-(OCHR$_1$CHR$_2$O)$_n$—, $C_1$-$C_6$-alkylene-Y$_1$—(CHR$_1$CHR$_2$O—)$_n$—, and —(CHR$_1$CHR$_2$O—)$_n$—;

n is 1-1000; and $Y_1$ is selected from the group consisting of —O—, —S—, —SO$_2$—, —N(SO$_2$R$_4$)—, and —N(COR$_4$)—;

Y is independently selected from the group consisting of —O-L-Q, —N(R$_4$)-L-Q, —N-(L-Q)$_2$, and —R$_4$;

wherein $R_4$ is selected from the group consisting of $C_1$-$C_{12}$-alkyl, substituted $C_1$-$C_{12}$-alkyl, $C_3$-$C_8$-cycloalkyl, $C_3$-$C_8$-alkenyl, and aryl; and Q is a group that comprises an ethylenically unsaturated polymerizable group;
with the proviso that the monomer molecules each comprise at least one Q group, and ii) at least one residue of one chromophoric monomer structure depicted by Ic or Id below or a combination thereof:

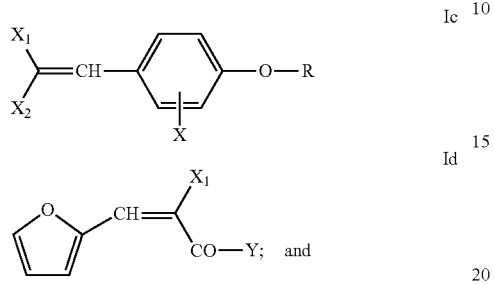

b) a cosmetically acceptable carrier,
wherein the polymer comprises residues of monomer Ia and residues of at least one of Ib Ic, and Id,
when the polymer does not include Formula Ib, the polymer includes at least one other ethylenically unsaturated copolymerized monomer selected from n-butyl acrylate, methyl methacrylate, ethyl methacrylate, or methacrylic acid, and
said residues are present in a ratio of Ia/In by weight of about 99/1 to about 60/40, where In is Ib, Ic, Id, or any combination thereof.

2. The composition according to claim 1, wherein said residues are present in a ratio of Ia/In by weight of about 99/5 to about 85/15, where In is Ib, Ic, and Id or any combination thereof.

3. A polymeric UV absorbing composition, comprising a UV absorbing polymer, comprising at least one residue of a chromophoric monomer structure depicted by Ia or Ib below or a combination thereof:

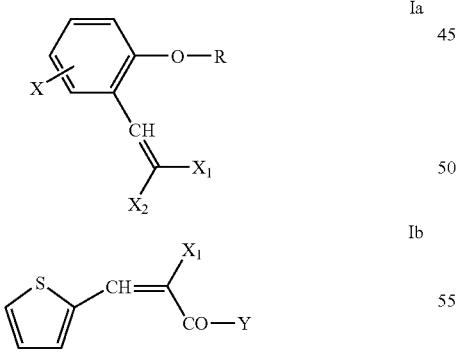

wherein X is hydrogen or one or two groups selected from the group consisting of hydroxy, $C_1$-$C_6$-alkyl, halogen, and —OR';
$X_1$ and $X_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;
R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$-alkenyl, —(CHR$_1$CHR$_2$O—)$_n$—R$_3$, and -L-Q;
wherein $R_1$ and $R_2$ are independently selected from the group consisting of hydrogen and $C_1$-$C_6$-alkyl;
$R_3$ is selected from the group consisting of hydrogen, $C_1$-$C_6$-alkyl, $C_1$-$C_6$-alkanoyl, aroyl, and aryl;
L is a divalent organic radical selected from the group consisting of $C_1$-$C_6$-alkylene-O—, $C_1$-$C_6$-alkylene-N(R$_1$)—, arylene-$C_1$-$C_6$-alkylene-O—, arylene-$C_1$-$C_6$-alkylene-(NR$_1$)—, arylene-(OCHR$_1$CHR$_2$O)$_n$—, $C_1$-$C_6$-alkylene-Y$_1$— (CHR$_1$CHR$_2$O—)$_n$—, and —(CHR$_1$CHR$_2$O—)$_n$—;
n is 1-1000; and
$Y_1$ is selected from the group consisting of —O—, —S—, —SO$_2$—, —N(SO$_2$R$_4$)—, and —N(COR$_4$)—;
Y is independently selected from the group consisting of —O-L-Q, -N(R$_4$)-L-Q, —N— (L-Q)$_2$, and —R$_4$;
wherein $R_4$ is selected from the group consisting of $C_1$-$C_{12}$-alkyl, substituted $C_1$-$C_{12}$-alkyl, $C_3$-$C_8$-cycloalkyl, $C_3$-$C_8$-alkenyl, and aryl; and
Q is a group that comprises an ethylenically unsaturated polymerizable group;
with the proviso that the monomer molecules each comprise at least one Q group; and
a cosmetically acceptable carrier.

4. The composition according to claim 3, wherein said composition contains a latex emulsion polymer.

5. The composition according to claim 4, wherein said polymeric emulsion includes a latex dispersion of the UV absorbing polymer.

6. A polymeric UV absorbing composition, comprising a UV absorbing polymer, comprising:
a) at least one residue of a chromophoric monomer structure depicted by Ia or Ib below or a combination thereof:

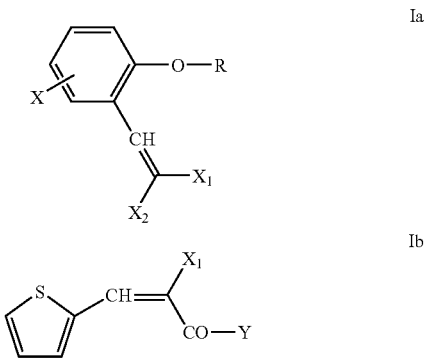

wherein X is hydrogen or one or two groups selected from the group consisting of hydroxy, $C_1$-$C_6$-alkyl, halogen, and —OR';
$X_1$ and $X_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;
R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$-alkenyl, —(CHR$_1$CHR$_2$O—)$_n$—R$_3$, and -L-Q;
wherein $R_1$ and $R_2$ are independently selected from the group consisting of hydrogen and $C_1$-$C_6$-alkyl;
$R_3$ is selected from the group consisting of hydrogen, $C_1$-$C_6$-alkyl, $C_1$-$C_6$-alkanoyl, aroyl, and aryl;

L is a divalent organic radical selected from the group consisting of $C_1$-$C_6$-alkylene-O—, $C_1$-$C_6$-alkylene-N(NR$_1$)—, arylene- $C_1$-$C_6$-alkylene-O—, arylene-$C_1$-$C_6$- alkylene- N(NR$_1$)—, arylene-(OCHR$_1$CHR$_2$O)$_n$—, $C_1$-$C_6$-alkylene-Y$_1$—(CHR$_1$CHR$_2$O—)$_n$—, and —(CHR$_1$CHR$_2$O—)$_n$—;

n is 1-1000; and

Y$_1$ is selected from the group consisting of —O—, —S—, —SO$_2$—, —N(SO$_2$R$_4$)—, and —N(COR$_4$)—;

Y is independently selected from the group consisting of —O-L-Q, -N(R$_4$)-L-Q, —(L-Q)$_2$, and —R$_4$;

wherein R$_4$ is selected from the group consisting of $C_1$-$C_{12}$-alkyl, substituted $C_1$-$C_{12}$-alkyl, $C_3$-$C_8$-cycloalkyl, $C_3$-$C_8$-alkenyl, and aryl; and Q is a group that comprises an ethylenically unsaturated polymerizable group;

with the proviso that the monomer molecules each comprise at least one Q group, and b) at least one residue of one chromophoric monomer structure depicted by Ic or Id below or a combination thereof

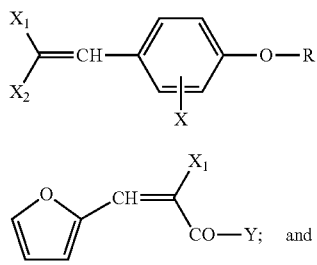

a cosmetically acceptable carrier.

7. The composition according to claim 6, wherein said composition contains a latex emulsion polymer.

8. The composition according to claim 7, wherein said polymeric emulsion includes a latex dispersion of the UV absorbing polymer.

9. A chromophoric monomer comprising a structure depicted by Formula Ib.

10. A composition, comprising a latex emulsion and a UV absorbing polymer, comprising at least one residue of a chromophoric monomer structure depicted by Ia or Ib below or a combination thereof:

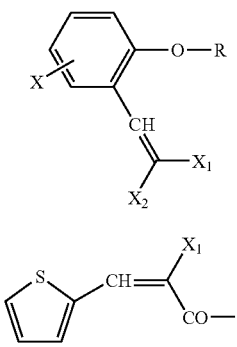

wherein X is hydrogen or one or two groups selected from the group consisting of hydroxy, $C_1$-$C_6$-alkyl, halogen, and —OR';

X$_1$ and X$_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;

R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$alkenyl, —(CHR$_1$CHR$_2$O—)$_n$—R$_3$, and -L-Q;

wherein R$_1$ and R$_2$ are independently selected from the group consisting of hydrogen and $C_1$-$C_6$-alkyl;

R$_3$ is selected from the group consisting of hydrogen, $C_1$-$C_6$-alkyl, $C_1$-$C_6$-alkanoyl, aroyl, and aryl;

L is a divalent organic radical selected from the group consisting of $C_1$-$C_6$-alkylene-O—, $C_1$-$C_6$-alkylene-N(R$_1$)—, arylene-$C_1$-$C_6$-alkylene-O—, arylene-$C_1$-$C_6$-alkylene-(NR$_1$)—, arylene-(OCHR$_1$CHR$_2$O)$_n$—, $C_1$-$C_6$-alkylene-Y$_1$—(CHR$_1$CHR$_2$O——)$_n$—, and —(CHR$_1$CHR$_2$O—)$_n$—;

n is 1-1000; and

Y$_1$ is selected from the group consisting of —O—, —S—, —SO$_2$-, —N(SO$_2$R$_4$)—, and —N(COR$_4$)—;

Y is independently selected from the group consisting of —O-L-Q, -N(R$_4$)-L-Q, —N —(L-Q)$_2$, and —R$_4$;

wherein R$_4$ is selected from the group consisting of $C_1$-$C_{12}$-alkyl, substituted $C_1$-$C_{12}$-alkyl, $C_3$-$C_8$-cycloalkyl, $C_3$-$C_6$-alkenyl, and aryl; and Q is a group that comprises an ethylenically unsaturated polymerizable group;

with the proviso that the monomer molecules each comprise at least one Q group.

11. A composition, comprising a latex emulsion and a UV absorbing polymer, comprising:

a) at least one residue of a chromophoric monomer structure depicted by Ia or Ib below or a combination thereof:

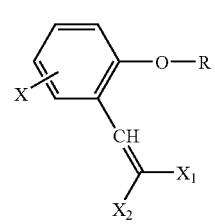

wherein X is hydrogen or one or two groups selected from the group consisting of hydroxy, $C_1$-$C_6$-alkyl, halogen, and —OR';

X$_1$ and X$_2$ are independently selected from the group consisting of cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl, and —COY;

R and R' are independently selected from the group consisting of hydrogen, $C_1$-$C_{12}$-alkyl, substituted $C_1$-$C_{12}$-alkyl, aryl, $C_3$-$C_8$-cycloalkyl, $C_3$-$C_8$-alkenyl, -(CHR$_1$CHR$_2$O—)$_n$-R$_3$, and -L-Q;

wherein R$_1$ and R$_2$ are independently selected from the group consisting of hydrogen and $C_1$-$C_6$-alkyl;

R$_3$ is selected from the group consisting of hydrogen, $C_1$-$C_6$-alkyl, $C_1$-$C_6$-alkanoyl, aroyl, and aryl;

L is a divalent organic radical selected from the group consisting of $C_1$-$C_6$-alkylene-O—, $C_1$-$C_6$-alkylene-N($R_1$)—, arylene-$C_1$-$C_6$-alkylene-O—, arylene-$C_1$-$C_6$-alkylene-(N$R_1$)—, arylene-(OCH$R_1$CH$R_2$O)$_n$—, $C_1$-$C_6$-alkylene-$Y_1$—(CH$R_1$CH$R_2$O—)$_n$—, and —(CH$R_1$CH$R_2$O—)$_n$—;

n is 1-1000; and $Y_1$ is selected from the group consisting of —O—, —S—, -SO$_2$—, —N(SO$_2$R$_4$)—, and —N(COR$_4$)—;

Y is independently selected from the group consisting of —O—L-Q, -N(R$_4$)-L-Q, —N—(L-Q)$_2$, and —R$_4$;

wherein R$_4$ is selected from the group consisting of $C_1$-$C_{12}$-alkyl, substituted $C_1$-$C_{12}$-alkyl, $C_3$-$C_8$-cycloalkyl, $C_3$-$C_8$-alkenyl, and aryl; and Q is a group that comprises an ethylenically unsaturated polymerizable group;

with the proviso that the monomer molecules each comprise at least one Q group, and b) at least one residue of one chromophoric monomer structure depicted by Ic or Id below or a combination thereof

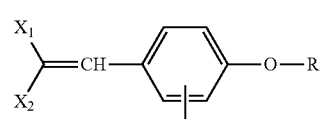

Ic

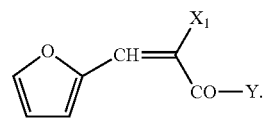

Id

\* \* \* \* \*